(12) United States Patent
Abjanic et al.

(10) Patent No.: US 7,111,076 B2
(45) Date of Patent: Sep. 19, 2006

(54) SYSTEM USING TRANSFORM TEMPLATE AND XML DOCUMENT TYPE DEFINITION FOR TRANSFORMING MESSAGE AND ITS REPLY

(75) Inventors: John B. Abjanic, San Diego, CA (US); David A. Marlatt, San Diego, CA (US)

(73) Assignee: Intel Corporation, Santa Clara, CA (US)

( * ) Notice: Subject to any disclaimer, the term of this patent is extended or adjusted under 35 U.S.C. 154(b) by 496 days.

(21) Appl. No.: 09/741,807

(22) Filed: Dec. 22, 2000

(65) Prior Publication Data

US 2003/0069975 A1    Apr. 10, 2003

Related U.S. Application Data

(63) Continuation-in-part of application No. 09/566,800, filed on May 8, 2000, which is a continuation-in-part of application No. 09/562,104, filed on May 1, 2000, and a continuation-in-part of application No. 09/549,041, filed on Apr. 13, 2000, now Pat. No. 6,732,175.

(51) Int. Cl.
G06F 15/16    (2006.01)

(52) U.S. Cl. ...................... 709/246; 709/201

(58) Field of Classification Search ............. 709/227, 709/246, 201, 217, 218, 219, 230, 225; 707/10; 717/136; 715/513
See application file for complete search history.

(56) References Cited

U.S. PATENT DOCUMENTS 5,218,676 A * 6/1993 Ben-Ayed et al. .......... 709/240
6,278,697 B1 * 8/2001 Brody et al. ................ 370/310
6,279,001 B1 * 8/2001 DeBettencourt et al. ...... 707/10
6,286,035 B1 * 9/2001 Gillis et al. ................. 709/206
6,430,624 B1 * 8/2002 Jamtgaard et al. .......... 709/246
6,477,646 B1 * 11/2002 Krishna et al. ............. 713/189
6,507,856 B1 * 1/2003 Chen et al. ................. 715/513
6,510,464 B1 * 1/2003 Grantges et al. ............ 709/225
6,675,219 B1 * 1/2004 Leppinen et al. ........... 709/230
6,772,216 B1 * 8/2004 Ankireddipally et al. ... 709/230
6,772,413 B1 * 8/2004 Kuznetsov .................. 717/136

FOREIGN PATENT DOCUMENTS

GB    2348083 A  *  9/2000

OTHER PUBLICATIONS

Shermin Voshmgir, XML Tutorials, 1999, www.javacommerce.com/tutorial/xmlj/intro.htm, p. 20 and 31.*
Beck et al., "IBM WebSphere Everyplace Suite v1.1", Oct. 18, 2000, IBM, pp. 1-34.*
Lear, "XML Seen as Integral to Application Integration", Oct. 1999, IT Pro, pp. 12-16.*
"IBM Transcoding Technology: Achitecture," 6 pp., 1999.

* cited by examiner

*Primary Examiner*—Le Hien Luu
(74) *Attorney, Agent, or Firm*—Kacvinsky LLC

(57) ABSTRACT

An apparatus, such as a transforming switch, is provided that includes a transformer to transform a message from a first format to a second format, and a switch to switch the message to a selected server or processing node. The apparatus may also include a security accelerator to decrypt and encrypt messages and a validation accelerator to pre-validate the received messages.

16 Claims, 10 Drawing Sheets

SYSTEM USING TRANSFORM TEMPLATE AND XML DOCUMENT TYPE DEFINITION FOR TRANSFORMING MESSAGE AND ITS REPLY

CROSS-REFERENCE TO RELATED APPLICATIONS

This application is a continuation-in-part of U.S. application Ser. No. 09/566,800 filed May 8, 2000 entitled "SCALABLE NETWORK APPARATUS FOR CONTENT BASED SWITCHING OR VALIDATION ACCELERATION," which is a continuation-in-part of U.S. application Ser. No. 09/549,041 filed Apr. 13, 2000 now U.S. Pat. No. 6,732,175 entitled "A NETWORK APPARATUS FOR SWITCHING BASED ON CONTENT OF APPLICATION DATA" and U.S. application Ser. No. 09/562,104 filed May 1, 2000 entitled "A NETWORK APPARATUS FOR VALIDATING DOCUMENTS," all of which are incorporated herein by reference.

BACKGROUND

1. Field

The embodiments generally relate to computers and computer networks and in particular to a network apparatus for transformation, such as a transforming switch.

2. Background

XML, or eXtensible Markup Language v. 1.0 was adopted by the World Wide Web Consortium (W3C) on Feb. 10, 1998. XML provides a structured syntax for data exchange. XML is a markup language, like Hypertext Markup Language (HTML). Most markup languages, like HTML, are fixed markup languages. That is, the fixed markup languages, such as HTML, include a set of fixed tags for crafting a document. On the other hand, XML does not define a fixed set of tags, but rather, only defines a syntax or structured format through which users can define their own set of XML tags. There presently are a number of XML based languages which define their own set of tags using the XML syntax. XML has the further advantage because the actual data is separated from the presentation of the data, in contrast with HTML which combines these two items. As a result, XML has the potential to become a standard by which most computers, servers and applications will exchange or communicate data.

Due to the wide variety of data formats that are in use, including different XML languages, there is a need for a transformer to transform between the varying formats. Presently, transcoders or transformers are available to perform transformations. For example, IBM's Transcoding Technology and Microsoft's BizTalk BizMapper perform some format translation functions and typically reside on a server, such as an application server. However, the web server or the application server are typically overloaded with a variety of tasks. Taking on the extra job of transforming simply compounds this problem. Moreover, the functionality of these translators is quite limited.

BRIEF DESCRIPTION OF THE DRAWINGS

The foregoing and a better understanding of the present invention will become apparent from the following detailed description of exemplary embodiments and the claims when read in connection with the accompanying drawings, all forming a part of the disclosure of this invention. While the foregoing and following written and illustrated disclosure focuses on disclosing example embodiments of the invention, it should be clearly understood that the same is by way of illustration and example only and is not limited thereto. The spirit and scope of the present invention is limited only by the terms of the appended claims.

The following represents brief descriptions of the drawings, wherein.

DETAILED DESCRIPTION

I. Content Based Switching

Figure 1:
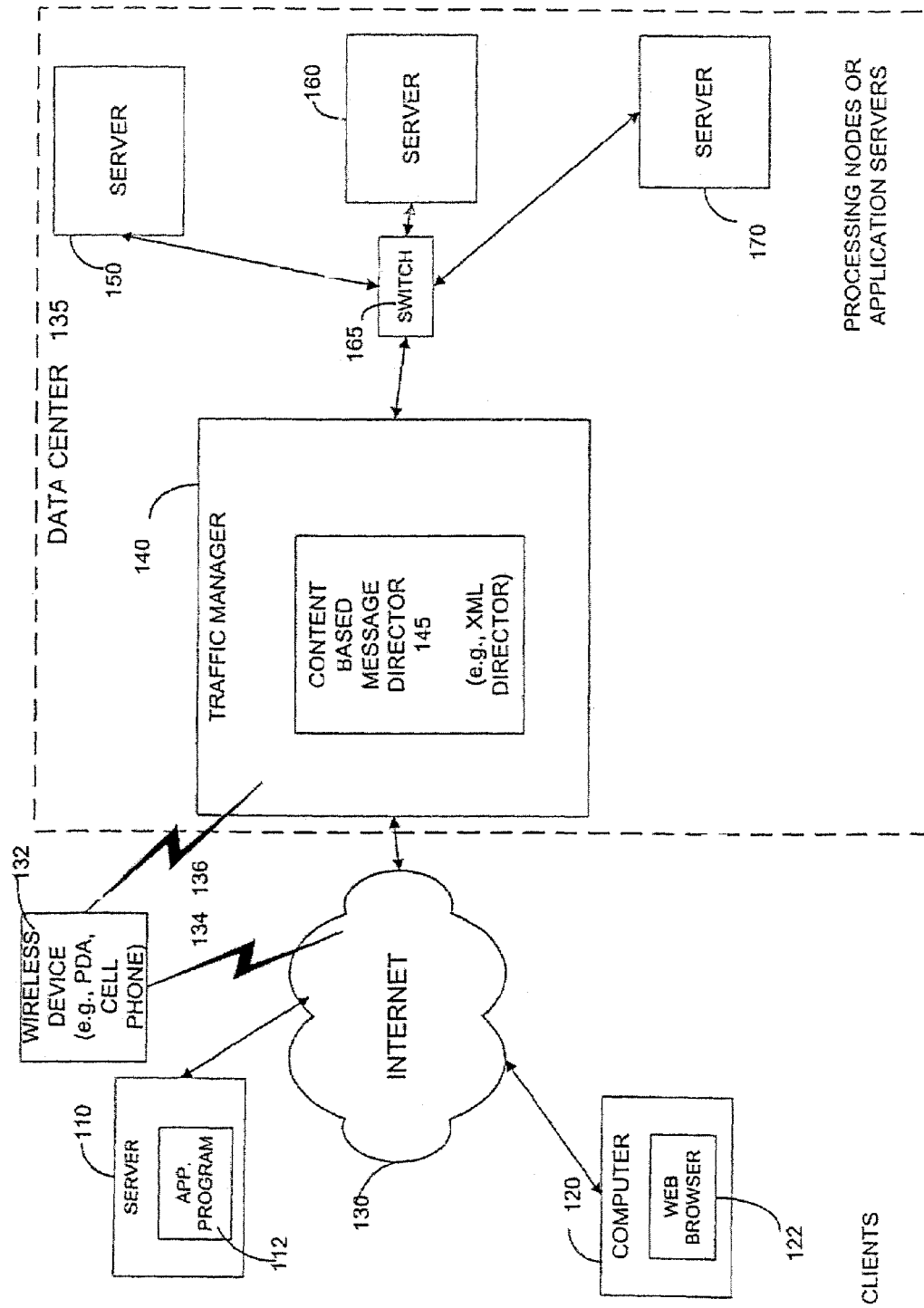
FIG. 1 is a block diagram of a network system according to an example embodiment.

Referring to the Figures in which like numerals indicate like elements, FIG. 1 is a block diagram of a network system according to an example embodiment. As shown in FIG. 1, a variety of clients may be coupled or connected to a data center 135 via a network, such as the Internet 130. The clients, for example, may include a server 110 that includes an application program 112, a computer 120 (such as a personal computer or laptop) that may include a web browser 122 and a wireless device 132, such as a personal digital assistant (PDA) or a wireless (or cellular) telephone. Wireless device 132 may be coupled to the Internet 130 or to a data center 135 via communications links 134 and 136, respectively. Links 134 and 136 each may include one or more of a wireless link, such as a cellular link or other link, or a wireline link. Each of the clients, including server 110, computer 120 and device 132 can send and receive messages over the Internet 130 and may use a variety of different protocols or transports.

The data center 135 is provided for sending, receiving and processing a wide variety of messages, requests, business transactions, purchase orders, stock quotes or stock trades, and other information. The data center 135 includes several processing nodes, such as servers, including server 150, server 160 and server 170 for handling the various orders, business transactions and other requests. The different servers in data center 135 may be allocated to provide different services, or even different levels of services. According to an example embodiment, the clients and the data center 135 exchange business transaction information or other information by sending and receiving XML messages, which may include data provided in XML or in a XML based language, or messages based upon another type of structured syntax for data interchange.

The various servers, such as servers 150, 160 and 170, are coupled to a traffic manager 140 via a switch 165. Traffic manager 140 may perform a variety of functions relating to the management of traffic, including load balancing, for example, balancing the load of incoming messages or requests across the available servers according to some policy, such as round-robin, least number of connections, or other load balancing technique.

Referring to the clients again in FIG. 1, application program 112 may be a business program or a program for managing inventory, orders or other business transactions. For example, application program 112 may automatically and electronically detect that inventory has decreased below a threshold value and then automatically generate and send a purchase order to a supplier's server at data center 135 to request a shipment of additional supplies or inventory. Thus, server 110 may initiate, for example, a business-to-business (B2B) transaction by sending an electronic order to the supplier's remote server located at data center 135.

As a another example, web browser 122 may request web pages, business information or other information from a remote server, for example, located at data center 135. Web browser 122, may also send or post purchase orders, business transactions or other business information to a remote server, which may be located at data center 135. Wireless device 132 may receive information or data related to purchase orders, business transactions, web pages, stock quotes, game scores and the like from one or more remote servers, such as servers located at data center 135.

According to an embodiment, the server 110, computer 120 and wireless device 132 each may communicate or interchange data with one or more remote servers, such as servers 150,160 and 170, by sending and receiving XML data, which may be application data that is encoded or formatted according to the XML standard or according to one or more XML based languages.

According to an example embodiment, the traffic manager 140 includes a content based message director 145 to direct or switch messages to a selected server based upon the content of application data, such as business transaction information, which may be provided as XML data as an example. Traffic manager 140 and/or message director 145 may be software, hardware or a combination of both, and may even be provided on or as part of a network processor. It should be noted that director 145 may operate by itself, or as part of a larger network apparatus, such as part of a traffic manager 140.

According to an example embodiment, because of the advantages of XML, application data can advantageously exchanged between the servers of data center 135 and one or more clients or computing nodes by sending and receiving messages that include application data that is encoded or formatted according to the XML standard. Therefore, according to an embodiment, director 145 may be a XML director because it directs or switches the incoming message to a particular server based upon the XML data in the message. The XML data preferably complies with the format or syntax required by the XML standard. A document that uses tag formats, such as start tags and end tags, and other syntax or markup data that complies with the XML standard is considered to be a "well-formed" XML document.

Therefore, in an exemplary embodiment, content based message director 145 is a XML director. However, it should be understood that director 145 can direct or switch messages having basically any type of structured syntax, including any type of markup language.

An advantageous aspect of the embodiment of the traffic manager 140 and director 145 shown in FIG. 1 is that the traffic manager 140 and the director 145 are located in front of the one or more application servers or processing nodes. By locating the traffic manager 140 and director 145 in a computer, server or computing system in front of the processing nodes or servers (as shown in FIG. 1), for example, coupled between the network 130 and the servers, the traffic management functionality and the functionality of the director 145 can be off-loaded from an application server to a separate and/or dedicated network apparatus or network system. This can advantageously relieve the processing nodes or application servers from this additional processing overhead.

Alternatively, the director 145 may include a built-in switch with a plurality of output ports (physical ports), with a server coupled to each physical output port. In such case, a group of servers may have the same IP address or Media Access Control (MAC) address, or could have different addresses. The director 145 then would simply output or switch or forward the packet, including the message containing the XML business transaction information, via one of the physical output ports to a particular server. Regardless whether the director 145 includes a built-in switch or uses switch 165 to switch the messages to the servers, the director 145 switches or directs the messages to various servers. Switch 165 and director 145 may also switch the packet based upon other information in the packet, such as a source address or destination address.

Figure 2:
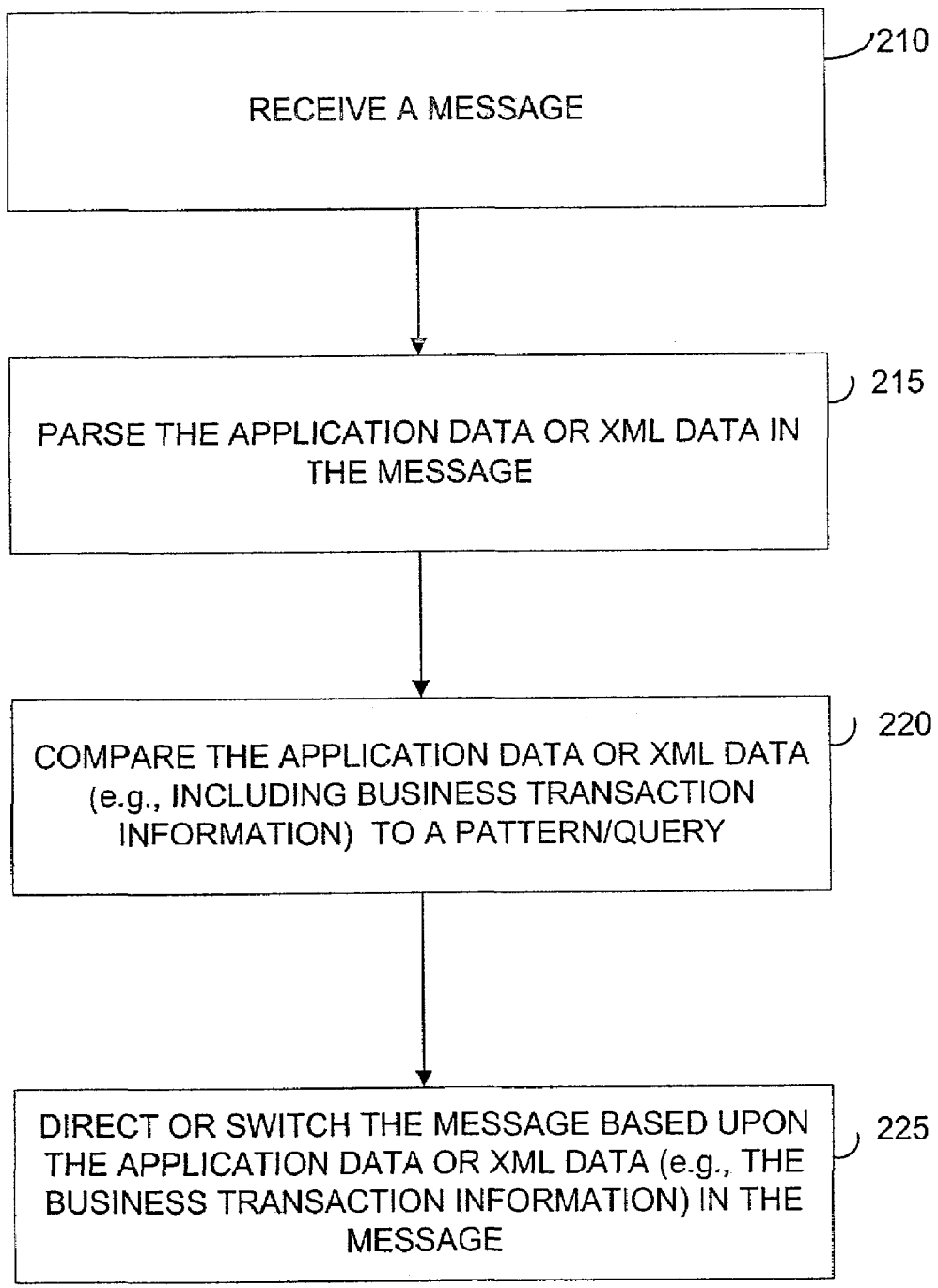
FIG. 2 is a flow chart illustrating an operation of content based message director according to an example embodiment.

FIG. 2 is a flow chart illustrating an operation of content based message director according to an example embodiment. At block 210, the director 145 receives a message. The message may be sent over any transport or protocol(s), such as Transmission Control Protocol (TCP), File Transfer Protocol (FTP), Simple Mail Transfer Protocol (SMTP), Wireless Application Protocol (WAP, which may be used to send and receive information with wireless devices), Hypertext Transfer Protocol (HTTP), etc. The general teachings and the operation of the invention are not dependent upon any particular transport or protocol, but rather are transport-independent.

A HTTP post is an example of a message. The format for an HTTP post message (or HTTP request) may be presented as:

request-line (the URL); identifies a program for processing the message headers (0 or more)
<blank line>
body (the application data or the XML data; only for a POST)

Here's an example:

```
POST www;acme.com/purchasing/order.cgi HTTP/1.1
Content-Type:text/xml
Content-Length: 1230
User-Agent: Cern-Line Mode/2.15
Date: 3/27/00
<XML>
        <From>intel.com</From>
        <To>bookstore.com</To>
        <PurchaseBook>
                <ISBN>02013798233</ISBN>
                <PurchaseAmount>98</PurchaseAmount>
        </PurchaseBook>
</XML>
```

In this example, the URL (or request line) is provided in a request line to identify a program or application to process the message. Several header lines (Content-type, Content-length, date, etc.) make up an HTTP header. The application data is provided after the HTTP header, and in this example is provided as XML data. A start tag <XML>, and </XML>, an end tag, identify the start and end, respectively, of the application data (or XML data). This XML application data is also referred to as a XML document. The XML document includes markup characters (or tags) which describe data, and data characters. As an example, a "To" element of the above XML document is written as: <To>bookstore.com</To>. Where<To> is a start Tag and </To> is an end tag, which are markup characters because they describe the XML data characters (bookstore.com). The business transaction information describes the business transaction (To, From, items purchased, purchase amount, quantity, etc.), and is not included in the URL, the HTTP header, or any other header, such as an IP header, TCP header, of the envelope used for sending the message. These are merely examples of the types of business transaction information in a message upon which the director 145 can analyze and make routing or switching decisions for the message.

At block 215 of FIG. 2, the director 145 (FIG. 1) parses all or part of the application data (the XML data in this example) and can check to ensure that the XML document or application data is well formed. For example, the director 145 may check to make sure at least a portion of the XML document meets the so-called well-formedness constraints or requirements in the XML specification or standard. Parsing generally refers to the process of categorizing the characters or XML data that make up the XML document as either markup (e.g., <To>) or character data (e.g., bookstore.com).

At block 220 of FIG. 2, the application data or XML data, including markup characters and/or character data, is then compared to one or more configuration patterns or queries, which may be stored in the director 145, to determine if there is a match. According to an embodiment, the configuration patterns may be dynamically changed or updated by a user or by a program or application. For example, a program may detect the failure of one or more servers and/or detect the response time of servers, and then update the configuration pattern to account for these changes in the network, for example, to redirect certain messages from busy servers to servers which are less busy, or from servers which have failed to the available servers.

At block 225, if there is a match between the content of the application data of a message, which may include the business transaction information which may be provided as XML data, and a configuration pattern or query, then the director 145 directs or switches the message to the corresponding server or processing node in the data center, for example, wherein the message is directed to the specific server as indicated by the configuration pattern. If there are multiple matches, the director 145 can just direct the message based on the first match, or a load balancing policy can be used to balance messages among a group of servers. If there is no match, the message can be directed to a default server or can be blocked. Alternatively, the configuration pattern can also identify a certain pattern for which a message should be blocked from being forwarded. In this respect, the director 145 may also act as a filter to selectively pass or forward some messages while blocking others, based upon the application data.

For example, the director 145 may be configured to direct or switch messages based on the following configuration patterns or queries:

| Server | IP address | Port | XML pattern |
|---|---|---|---|
| S1 (e.g., 150) | 10.1.1.1 | 80 | To = bookstore.com |
| S2 (e.g., 160) | 10.1.1.2 | 80 | To = stockquote.com |
| S3 (e.g., 170) | 10.1.1.3 | 80 | To = computerstore.com |

Based on the above configuration patterns, the director 145 would direct a message to server S1 (having the IP address 10.1.1.1 and port 80) if the data for the To element of the business transaction information is bookstore.com. The message will be directed to server S2 (having an IP address 10.1.1.2 and port 80) if the data for the To element of the business transaction information is stockquote.com. And, the director 145 will direct any messages to server S3 if the data for the To element of the business transaction information is computerstore.com. Director 145 will translate a destination address and port number of the packet to the appropriate destination address and port number (i.e., to the address of the destination server), if necessary.

This advantageously allows different types of services (or different levels of service) to be provided for messages based on the content of the application data, such as the business transaction information, in the message. In this example, server S1 may be allocated to handle purchase orders for books sent to bookstore.com. Server S2 may be allocated to process requests for real-time stock quotes, while server S3 may be allocated to process purchase orders for computers sent to computerstore.com.

There are many examples where content based switching based upon the content of the application data or business transaction information can be used to offer different or differentiated services or even different or differentiated levels of services. As another example, the director 145 may be configured to direct or switch messages based on the following configuration patterns or queries:

| Server | IP address | Port | XML pattern |
|---|---|---|---|
| S1 (e.g., 150) | 10.1.1.1 | 80 | PurchaseAmount < $100 |
| S2 (e.g., 160) | 10.1.1.2 | 80 | $100 < PurchaseAmount < $1000 |
| S3 (e.g., 170) | 10.1.1.3 | 80 | $1000 < PurchaseAmount |
| S4 (not shown) | 10.1.1.4 | 80 | $1000 < PurchaseAmount |

In this example, messages for purchase orders are sent to server S1 if the purchase amount is less than $100; messages for purchase orders are sent to S2 if the purchase amount is less than $1000 and more than $100; and for the high dollar purchases, the messages for purchase orders for purchases greater than $1000 can be sent to either of two servers. In this fashion, the director 145 (FIG. 1) can direct or route received messages based on the content of the application data or business transaction information in the message. This allows web sites or electronic-businesses (e-businesses) to offer different or differentiated levels of services based on the content of the application data or transaction information.

In this particular example, two servers (S3 and S4) have been allocated to handle the highest dollar purchase orders. Thus, by specifically allocating greater resources (e.g., two or more servers as compared to just one server) for the higher dollar amount purchases as compared to the lower dollar purchases, an e-business operating at data center 135 can provide a higher level of service for purchase order messages having a higher dollar purchase amount. In this manner, director 145 can switch or direct messages to another network device or to a specific server based upon a wide variety of business transaction information or application data.

II. Validation Acceleration

Figure 3:
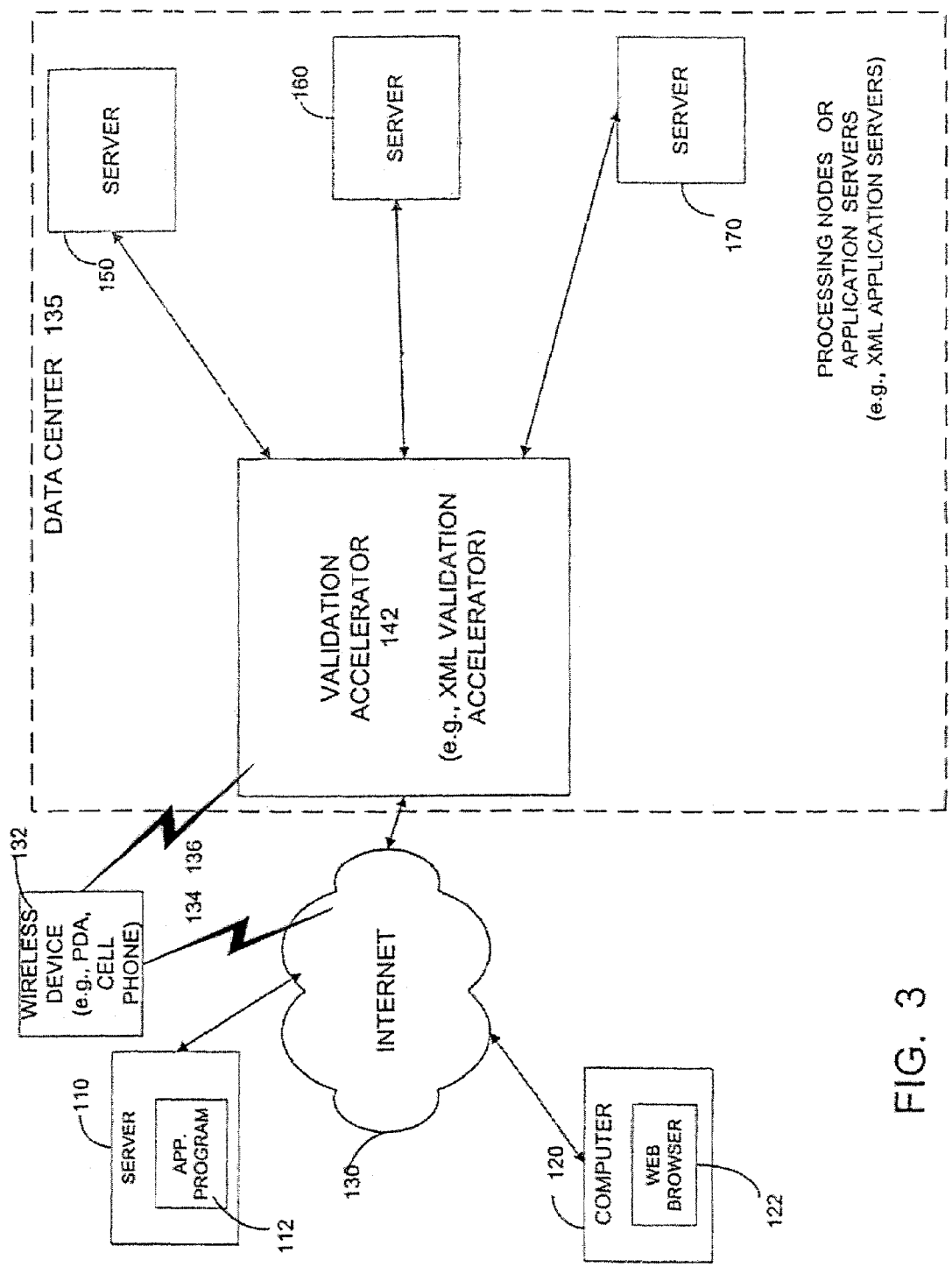
FIG. 3 is a block diagram illustrating a network system including a validation accelerator according to an example embodiment.

FIG. 3 is a block diagram illustrating a network including a validation accelerator 142 according to an example embodiment. According to an advantageous embodiment, the data center 135 also includes a validation accelerator 142 to pre-validate received messages before the messages are sent to one of the application servers or processing nodes. According to an example embodiment, the validation accelerator 142 is provided as a network apparatus. In other words, according to an example embodiment, the validation accelerator 142 can be coupled between a network 130 and a plurality of processing nodes or application servers, such as servers 150,160 and 170. Providing the validation accelerator 142 as a network apparatus that may be separate from the application servers allows the computationally expensive task of document validation to be off-loaded from the application servers to the validation accelerator 142. Alternatively, a plurality of validation accelerators 142 may be provided, with one validation accelerator 142 being provided for one or more application servers or other processing nodes.

As noted above, an XML document must be checked to ensure it meets the basic syntax and format of XML, for example, to determine whether the document is "well formed". In addition, the XML standard also optionally allows a document to be validated, which is a more rigorous check to determine if the structure or grammar of the XML document complies with structure or grammar required by the particular XML based language. XML allows a document to be validated against a validation template. A validation template defines the grammar and structure of the XML document, including required elements or tags, etc.

There can be many types of validation templates such as a document type definition (DTD) in XML or a schema, as examples. These two validation templates are used as examples to explain some features according to example embodiments. Many other types of validation templates are possible as well. A schema is similar to a DTD because it defines the grammar and structure which the document must conform to be valid. However, a schema can be more specific than a DTD because it also includes the ability to define data types, such as characters, numbers, integers, floating point, or custom data types, etc. In addition, unlike a DTD (under present standards), a schema may be required to be well formed. Thus, both the application data and the schema can both be parsed and checked for basic syntax or well-formedness. Therefore, at least for some applications, it is expected that schemas will possibly become more common than DTDs in the future.

As noted above, validating a received document against a validation template is optional according to the XML standard. If a document is to be validated against a particular validation template, the XML document will include validation instructions (or validation code) at the beginning of the document. One example of validation instructions can be a document type declaration, as commonly known in XML. Another example is a schema or a reference to an external schema. According to current XML, the validation instructions, such as document type declaration or schemas, etc. are an optional area of the document that declares the structure, element types, attributes, etc. of the validation template. To be a valid document, the structure and grammar of the application data in the document must match the structure and grammar defined by the validation template, for example, if validation instructions are included in the document. The validation template can be provided internal to (or within) the document and/or external to the document.

Figure 4:
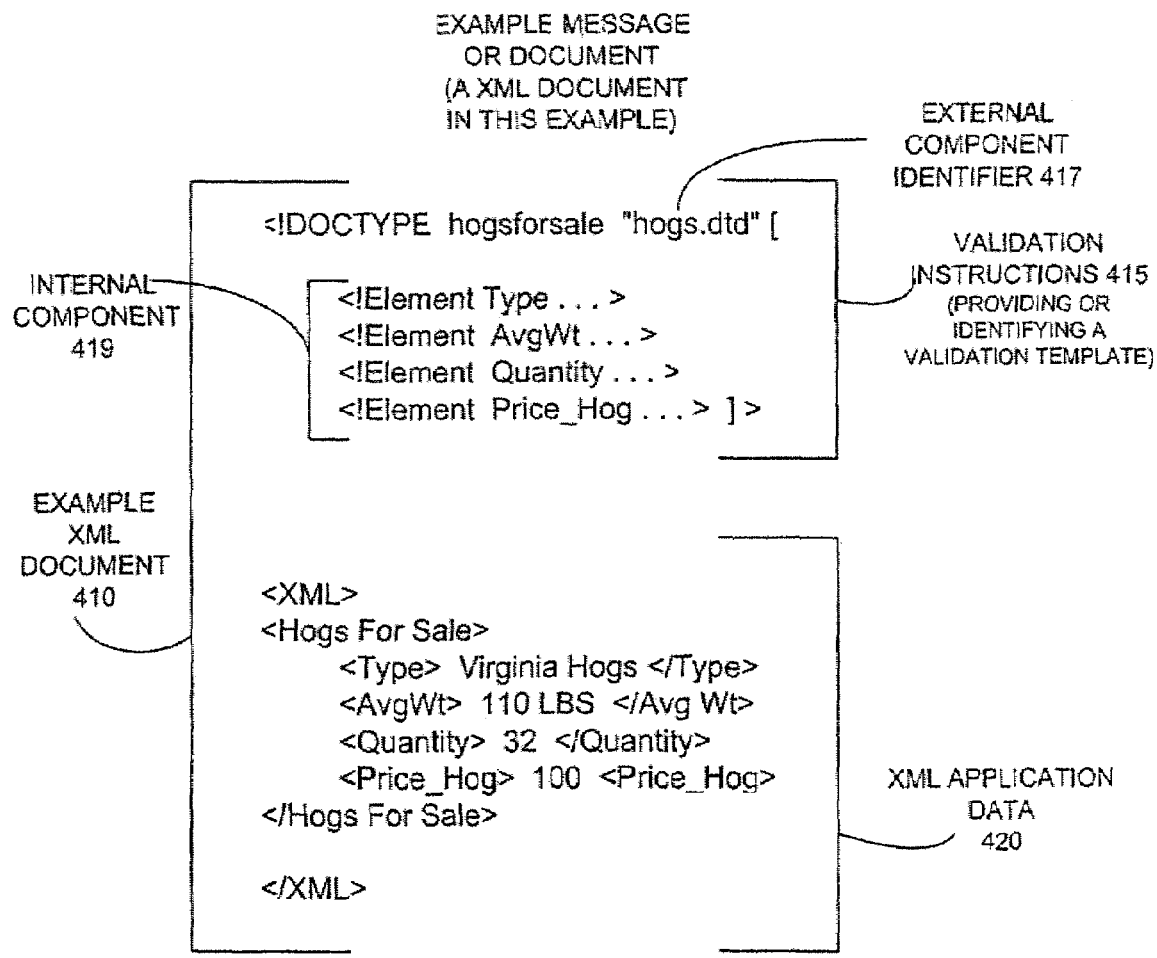
FIG. 4 is a diagram illustrating an example message according to an example embodiment.

FIG. 4 is a diagram illustrating an example message according to an example embodiment. The example message shown in FIG. 4 includes an XML document 410. XML document 410 includes XML application data 420, for example, including business transaction information, and validation instructions 415.

The application data 420 is the application data that will be processed by an application server. The application data 420 may include, for example, business transaction information, such as a list items to be purchased, prices, quantities or other specific details of a transaction or a request for information, such as a request for stock quote, transaction details, etc.

According to an embodiment, the presence of one or more validation instructions 415 indicates that the document may be validated before processing the application data 420 based on a validation template provided within and/or identified by the validation instructions 415. In other words, according to an embodiment, the presence of validation instructions may indicate that the application data should be pre-validated at a network apparatus (such as validation accelerator 142) before passing the data to an application server for further processing. To indicate to the application server that the document or the application data has been validated, the validation instructions may be removed from the document and/or an indication, such as a comment or instruction in the data or a field set in the message, may be provided to indicate that the application data or message has been validated (i.e., pre-validated). According to current XML, document validation is optional, for example, by the application server, even when validation instructions 415 are present. However, it is possible that in the future, validation in XML or other languages may be required.

If the document should be associated with a validation template, such as a document type definition, schema, etc., for document validation, the document will typically include one or more validation instructions 415. The validation instructions 415 provide or identify the validation template or document type definition which defines the document structure and grammar, for example, elements, attributes, etc., to which the application data 420 of document 410 must conform. The validation template can include an internal component and/or an external component.

In this example shown, the validation instructions 415 or validation template are provided as a document type declaration. The validation instructions 415 begin with the DOCTYPE statement "<DOCTYPE hogsforsale . . . " which indicates that there is a validation template, which may be provided within the document, for example, as internal component 419, or provided external to the document, such as an external component identified as "hogs.dtd" 417 in this example. Therefore, in this example, the validation instructions 415 provide an internal component 419 of a validation template and an external component identifier 417 identifying an external component. The internal component 419 and the external component (not shown) together form the validation template for this document for validating the application data 420 for document 410. According to an embodiment, if validation is being performed, the presence of the DOCTYPE statement or other validation instructions typically will cause an application or application server to validate the application data 420 in the message against the validation template.

The internal component 419 of the validation template defines that a valid hosgsforsale document must include the following elements: type, avg wt, quantity and price/hog, etc. This is just an example.

In this example, the identifier "hogs.dtd" identifies an external entity or file which is an external component of the validation template. The external component can be located on a remote server or other location based on the external component identifier 417. The external component of the validation template (identified as "hogs.dtd") may include additional requirements on the structure or grammar of the application data 420 of the document 410. The external component identifier 417 may be provided as the complete address, or as a relative address or pointer, for example, relative to the address or location of the source or originating node of the message. For example, the "hogs.dtd" identifier listed in the validation instructions 415 may actually reference the "hogs.dtd" external component 417 which may be found at, for example: oasis.xml.org/farming/livestock/hogs.dtd. As noted above, examples of validation templates include a Document Type Definition for XML, a schema, etc.

Figure 5:
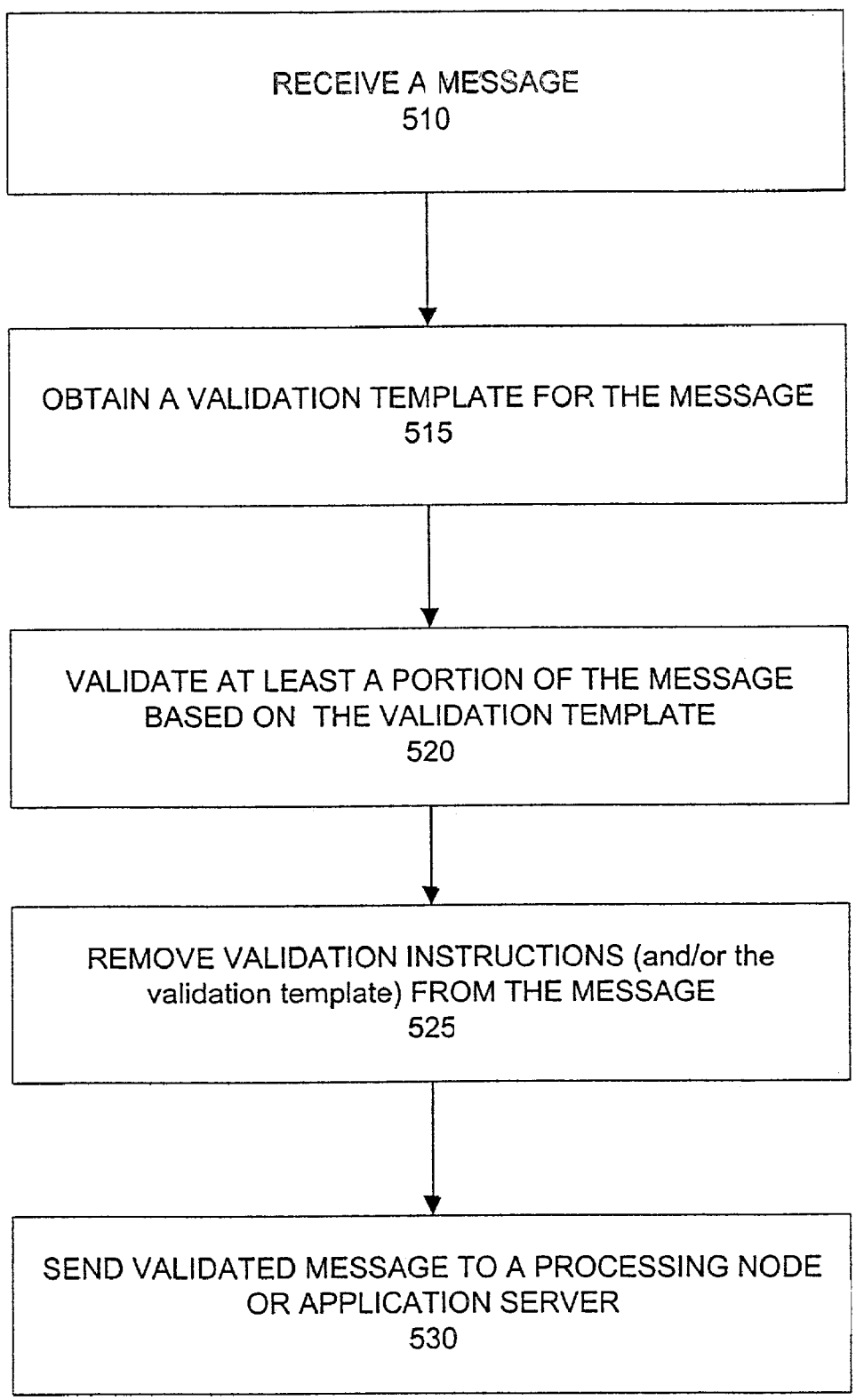
FIG. 5 is a flow chart illustrating an example operation of a validation accelerator according to an example embodiment.

FIG. 5 is a flow chart illustrating an example operation of a validation accelerator according to an example embodiment. At block 510, the validation accelerator 142 receives a message. The message may be sent over any transport or protocol(s), such as Transmission Control Protocol (TCP), File Transfer Protocol (FTP), Simple Mail Transfer Protocol (SMTP), Wireless Application Protocol (WAP), which may be used to send and receive information with wireless devices), Hypertext Transfer Protocol (HTTP), etc. The general teachings and the operation of the invention are not dependent upon any particular transport or protocol, but rather are transport-independent.

At block 515, a validation template is obtained by the validation accelerator 142 for validating the document or message, for example, for validating the application data 420 in the document 410, FIG. 4. This may include first determining if validation instructions are present in the document or message. If no validation instructions are present, then validation will not be performed. If validation instructions are present, the validation accelerator 142 then determines whether the validation template for the document is provided as an internal component and/or an external component based upon the syntax of or one or more statements in the validation instructions 415.

If the validation template is provided within the document as an internal component, the validation template is parsed from or separated from the remainder of the document. If the validation instructions 415 provide a external component identifier 417, then the validation accelerator 142 then retrieves or obtains the external component, for example, from a remote server or node.

At block 520 of FIG. 3, the validation accelerator 142 validates at least a portion of the message, for example, validates the application data 420, by comparing the structure and grammar of the application data 420 to the structure and grammar defined or required by the validation template.

At block 525, if the document or message is valid, the validation accelerator 142 then removes the (preferably all of the) validation instructions, including any statements that might cause the document to be validated, for example, a DOCTYPE statement, any internal component(s) of the validation template and any references or identifiers to external components of the validation template.

At block 530, the validated document with the validation instructions removed is then sent to an application server or other processing node for processing.

Alternatively (or in addition to removing the validating instructions), an indication can be added to the message indicating to the application server that the application data or message has already been validated (i.e., pre-validated). This pre-validation indication can be provided, for example, as a field in the message, as an instruction or comment in the application data itself, or using another technique. For example, In the XML specification, besides element tags, and data, there is something known as a processing instruction tag which allows information specific to an application to be embedded in an XML document. Processing instructions are not considered to be part of the character data content of an XML document, but they are always passed on to the XML application by the parser. The format is <? . . . ?> for the processing instruction tag. Thus, according to one embodiment, after the validation instructions (or the DTD or schema or reference thereto) has been removed, the following comment or instruction tag could be added near the beginning of the document (or other location): <? validated by intel?>.

Alternatively, a different destination address or port number can be used in the packet header to indicate that the XML message in the packet has been pre-validated. For example, instead of port 80, port 87 can be used as the destination port to indicate a pre-validated message for an XML document. These are just some example techniques that can be used to indicate to the server that the XML document has been already validated, or need not be re-validated.

By pre-validating the document and then removing the validation instructions from the document, and/or adding a pre-validation indication to the document or message, the expensive step of validation is off-loaded from the application server to a network apparatus, network appliance or other system, which may be referred to, for example, as the validation accelerator 142.

III. Transformation

Figure 6:
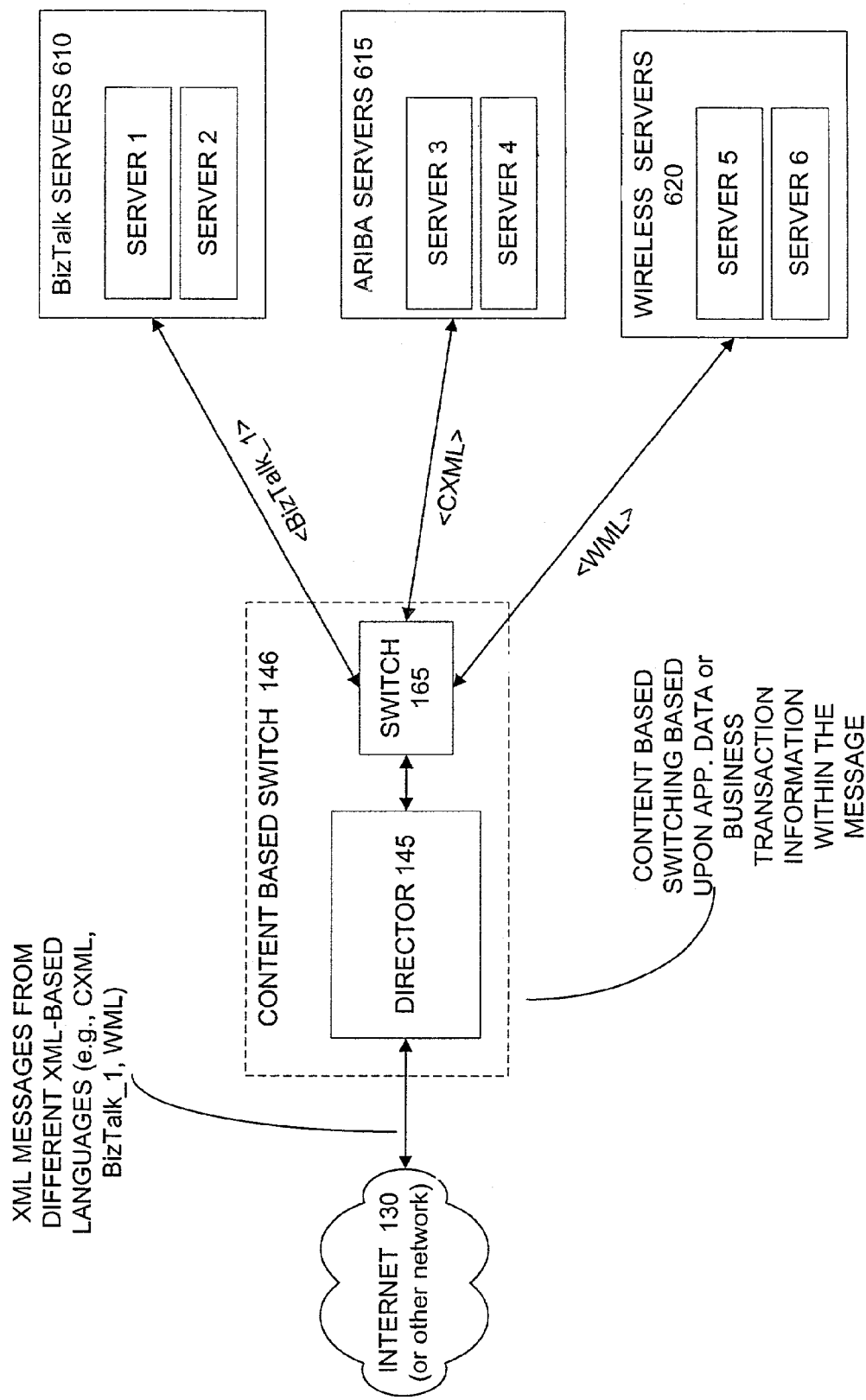
FIG. 6 is a block diagram illustrating another example operating environment for a content based message director according to an example embodiment.

FIG. 6 is a block diagram illustrating another example operating environment for a content based message director 145 according to an example embodiment. Message director 145 and switch 165 together may be considered as a content-based switch 146.

As noted above, XML does not define a fixed set of tags, but rather, only defines a syntax or structured format through which users can define their own set of tags or their own XML based language. In fact there are many different XML-based languages in use, each having a unique set of tags that define what elements should be provided to comply with that XML language.

An XML language can be defined by a validation template that may typically indicate the proper form for the tags, known in XML as a Document Type Definition (DTD). Schemas can also be used. For example, BizTalk by Microsoft Corp. includes one set of XML tags; CXML by Ariba Corp. includes its own set of tags; CBL by Commerce One includes another set of XML tags; While WML (Wireless Markup Language) defines yet another set of XML tags for the communication or interchange of data to and from a wireless device. Each of these XML-based languages includes a different or unique set of tags, and thus each is generally incompatible with the other languages. For example, a client sending data using CXML will not be able to properly communicate with a processing node or server that expects to receive data only provided according to CBL.

According to an advantageous aspect of the present invention, switch 146 can receive an XML message, compare the application data or business transaction information to the configuration pattern, and then switch the message to an appropriate processing node or server regardless of the type of XML-based language used by the message. Once the message director 145 of switch 146 is configured to detect or recognize one or more specific tags and corresponding data (for example, Purchase Amount >$100), the content based switch 146 can direct or route or switch the message based on the content of the application data, for example, based on the business transaction information provided as XML data, regardless of the type of XML-based language that is used by the message.

As shown in FIG. 6, there are three sets of servers coupled to the switch 165, including: a set of BizTalk servers 610 (including servers 1 and 2) which communicate data using an XML based language known as BizTalk; a set of Ariba servers 615 (including servers 3 and 4) which communicate data using the XML based language known as CXML; and a set of wireless servers 620 (including servers 5 and 6) which communicate data using only the XML based language known as Wireless Markup Language or WML. These are merely provided as examples.

Messages can arrive at switch 146 in a variety of different data formats including Electronic Data Interchange (EDI), a flat alpha-numeric file format, one or more XML languages or formats (such as WML, CXML, BizTalk, eBXML, etc.), HTML, etc. Certain client computers may be able to communicate using one type of data format (or very few types of formats), while application servers (such as servers 610, 615, 620) each may communicate using a different type of data format. In other words, to allow clients and servers to communicate with each other where different data formats are involved, a translation or transformation function should be provided to transform from a first format to a second format. Rather than providing the transformation function as part of the application server, an embodiment of the invention provides a transformation function as part of a switch or other network apparatus (for example, a transforming switch) which may be provided, for example, between a network or Internet 130 and one or more servers or processing nodes.

Figure 7:
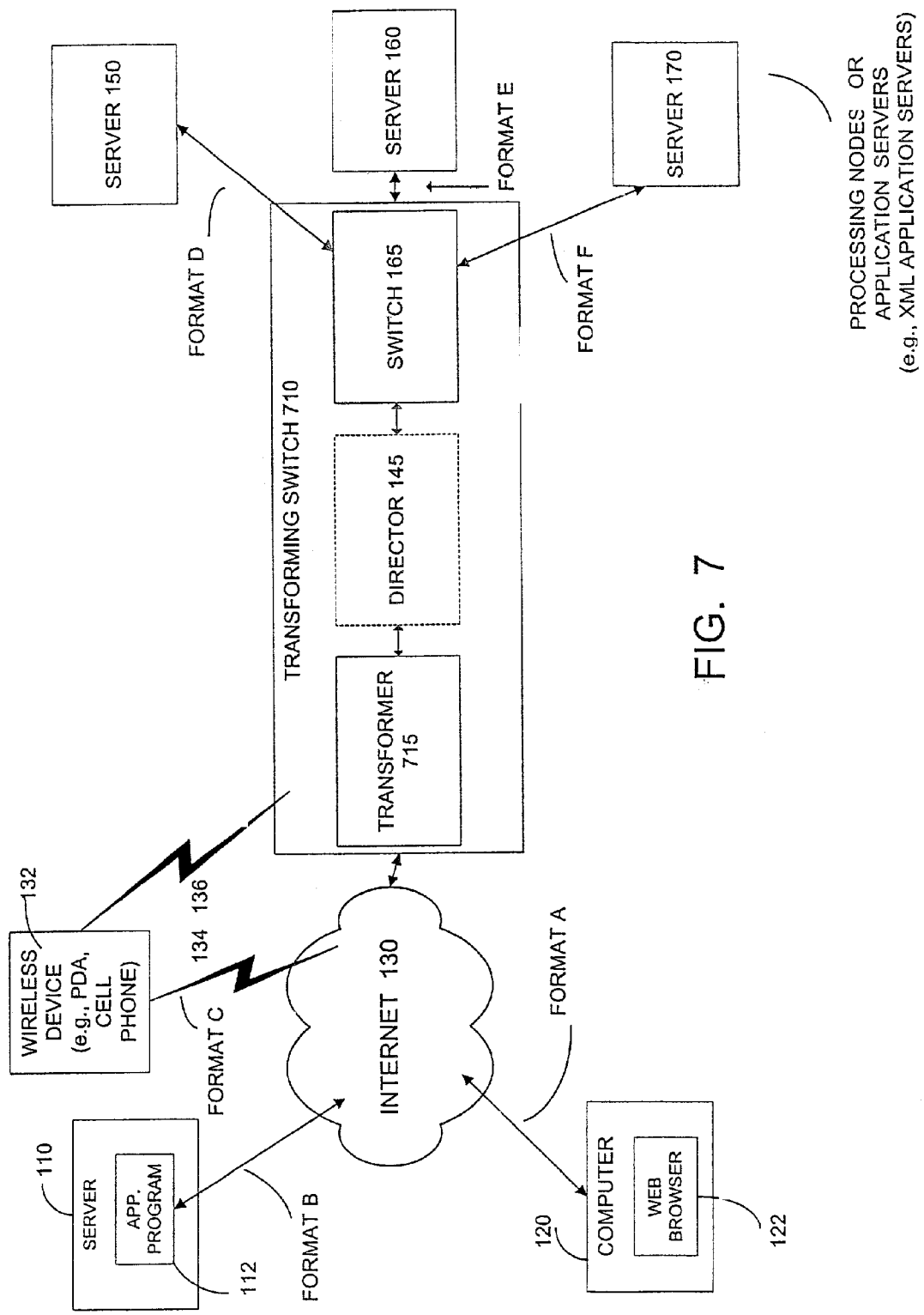
FIG. 7 is a block diagram illustrating a transforming switch according to an example embodiment.

FIG. 7 is a block diagram illustrating a transforming switch according to an example embodiment. Transforming switch 710 includes a transformer 715 to transform or translate at least a portion of a message from a first data format to a second data format or to a selected one of a plurality of second formats. Message Director 145, which may be optional in some embodiments, is coupled to the output of transformer 715. Message director 145 directs or switches messages to a selected server based upon the content of application data, such as business transaction information, which may be provided as XML data or data in another format. According to an example embodiment, message director 145 may output a switching decision to switch 165 based on the business transaction information of the message as compared to a pattern (or one or more patterns), as described above. Switch 165 then switches the transformed message to one of a plurality of output ports or to one of a plurality of servers (such as servers 150, 160 and 170) based on the decision or instructions from message director 145. Because content based message director 145 may be optional in some instances, switch 165 may switch the transformed message using address-based routing or switching techniques, such as switching to a particular output port of switch 165 based on source and/or destination address and port numbers provided in the message or provided in a header of a packet carrying the message.

Transformer 715 can transform messages between a variety of different data formats, as required. An example communication may include a request followed by a response, although the invention is not limited in this respect. For example, a first node may issue a request over network or Internet 130 that is received by a second node. The second node may send a response back to the first node. Both the request and response may typically be routed over the Internet or network 130 and transforming switch 710. The request and the response may both include data that may need to be transformed. The transforming switch receives the message, provided in one or more packets, determines if the data within the packet(s) needs to be transformed, performs any transformation that is required, and then forward the message via one or more packets.

There are four general cases involving transformations: A transform may be performed on just data in the request, on just data in the response, on data in the request and in the response, and in neither. This last case involves messages having data, if any, that is already in a format that is compatible with the receiving node, and thus, no transformation is necessary.

For example, web browser 122 of computer 120 may issue a request for a stock quote using a HTTP "Get" message, and be able to process data only in format A. The request may be sent via network 130 and switch 710 to server 150 without transformation, for example, because both server 150 and browser 122 are compatible with HTTP messages. Server 150 then issues the response having data (the stock quote) in format D. The data in format D may be placed in another HTTP message. While both browser 122 and server 150 are HTTP compatible, server 150 processes data in format D while browser 122 processes data in format A. Thus, transformer 715 within switch 710 would then transform the data in the response from format D to data format A and then forwards the response back to the web browser 122 over network 130.

In another example, in a business-to-business (B2B) transaction, server 150 obtains a blank invoice from server 110 via Internet or network 130 and switch 710. A software program on server 150 fills out or completes the received invoice and returns the completed invoice. The switch 710 receives the completed invoice from server 110 in format A in one or more packets, transforms the invoice from format A to format D, and then outputs the completed invoice to server 150 in format D, for example via one or more packets sent over Internet or network 130.

According to an example embodiment, switch 710 may establish a connection with a first node and then receive a message, including application data, etc. from the first node via one or more packets over the first connection. Switch 710 then performs any required transformation on the message, if any, and then establishes a second connection between the switch 710 and a second node. The transformed message is then switched or output as one or more packets over the second connection to the second node. Thus, the transforming switch 710 may operate as a network apparatus to receive or intercept messages, perform any format transformation on a portion of the message if required, and then switch or forward the message via one or more packets to a destination processing node. In many cases, the presence of the transforming switch and the fact that the data or message may be transformed in one or both directions may be transparent to one or both processing nodes.

Figure 8:
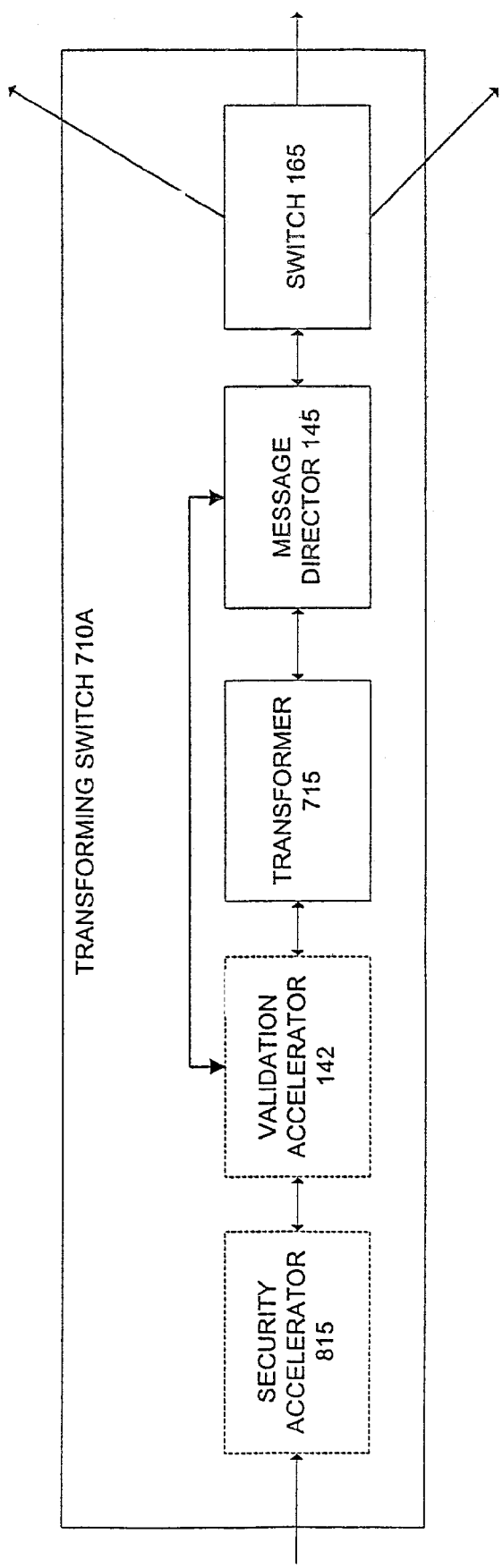
FIG. 8 is a block diagram illustrating a transforming switch according to another example embodiment.

FIG. 8 is a block diagram illustrating a transforming switch according to another example embodiment. Transforming switch 710A is similar to the transforming switch 710 shown in FIG. 7, as it includes a transformer 715, a message director 145 and a switch 165. The transforming switch 710A may further include two additional elements, including a security accelerator 815 and/or a validation accelerator 142.

As described above, the validation accelerator 142 validates at least a portion of the message (e.g., validates the application data 420, FIG. 4) by comparing the structure and grammar of the application data 420 to the structure and grammar defined or required by the validation template. If the document or message is valid, the validation accelerator 142 then optionally removes the validation instructions, including any statements that might cause the document to be validated (e.g., a DOCTYPE statement), any internal component(s) of the validation template and any references or identifiers to external components of the validation template. In addition, validation accelerator 142 may add to the message an indication indicating that the application data or message has already been validated (i.e., pre-validated). In the event that the validation instructions (e.g., validation template or a reference to an external validation template) are removed from the document, the validation accelerator 142 should pass the validation instructions (such as the reference to the validation template) to the transformer 715 (e.g., to be used to identify the correct transformation template). Rather than stripping out or removing the validation instructions, the validation instructions may be left in the message to be used to perform the transformation or to determine whether a transform is required and to identify the type of transform that should be performed. The switch 710 may also add to the message an indication that the message has been transformed or an indication that the message has been transformed and validated, so as to inform a processing node that receives the message that these functions, transformation and validation, have already been performed and need not be repeated.

Therefore, as shown in the example embodiment of FIG. 8, validation accelerator 142 validates the message or document before it is transformed. This ensures that the message has the correct format and grammar before transforming the message. In addition (or in the alternative), validation accelerator 142 may validate the message after it has been transformed to the new data format. (e.g., the validation accelerator 142 may receive a copy of the transformed message from message director 145, validate it and then notify the director 145 of its validity before the director 145 outputs the message to switch 165 for switching). The post-transformation message validation ensures that no errors occurred during the transformation. The second validation is not necessary. Validation can be performed before transformation, after transformation, both before and after transformation, or not at all.

Security accelerator 815 encrypts outgoing messages and/or decrypts incoming messages received from the network 130. According to an embodiment, the security accelerator 815 may be a Secure Sockets Layer (SSL) accelerator. The security accelerator 815 allows the security related tasks such as encryption and/or decryption to be off-loaded from the application server to the accelerator 815. Security accelerator 815 is optional.

The transforming switch 710 or 710A may comprise one or more boxes, where a box could be a computer system, a network apparatus, a network appliance, a computer chassis where cards or blades can be plugged in, etc. For example, each of the functional elements of transforming switch 710A (security accelerator 815, validation accelerator 142, transformer 715, message director 145 and switch 165) may each be provided in a separate computer or box (with its own processor or processors, memory, etc.). Several of the functional elements of transforming switch 710A can be combined into one or more computer systems or boxes, for example, sharing one or more processors, memory, bus, etc. All of the functional elements of transforming switch 710A may be provided within a single box, computer, or network apparatus such as a single box or chassis with each functional element provided as a separate software program. Alternatively, transforming switch 710 or 710A can be provided on a computer chassis, with one or more of the functional elements being provided as separate cards or blades that plug into the chassis. These are just a few examples, and the invention is not limited to these examples.

Figure 9:
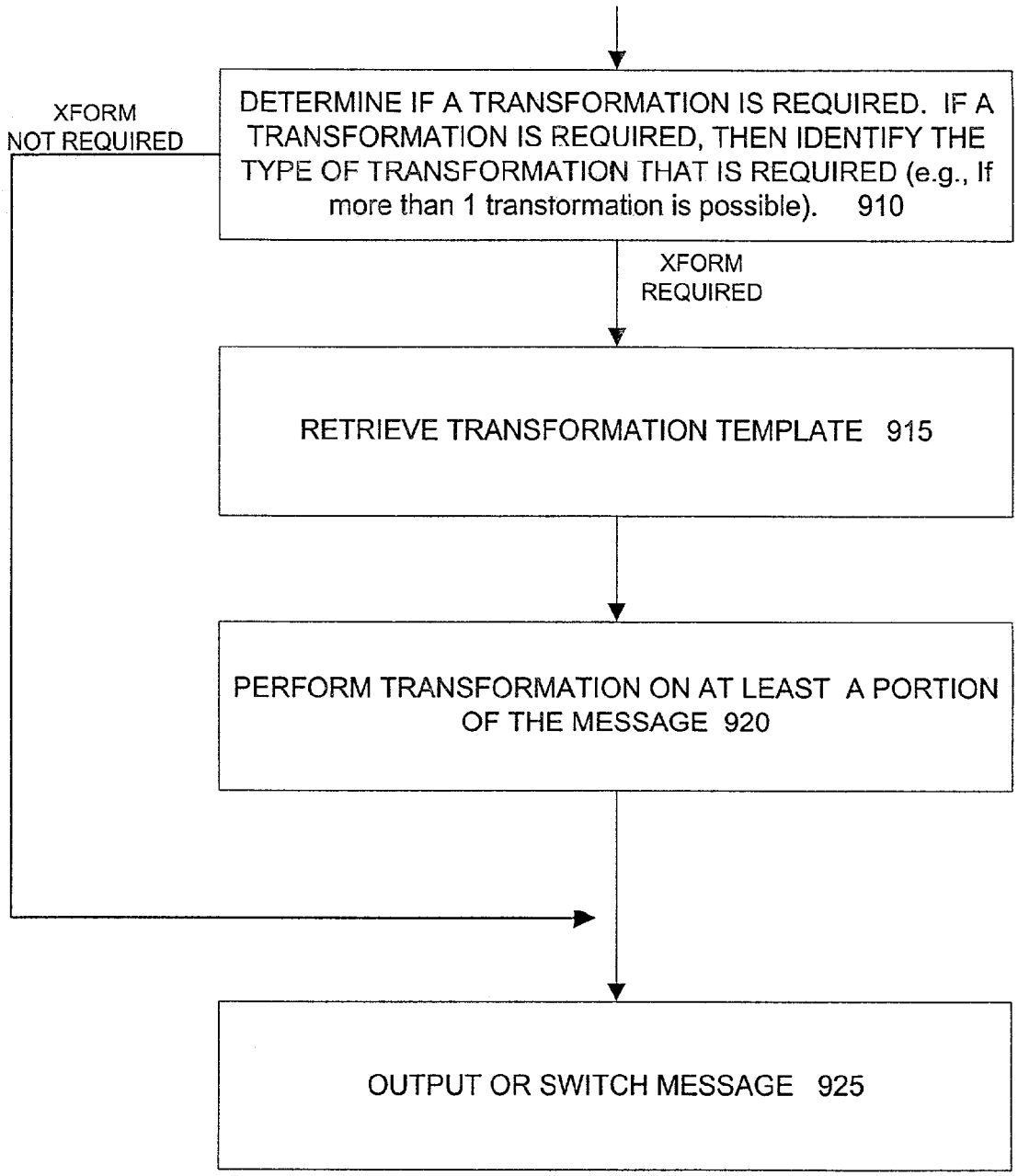
FIG. 9 is a flow chart illustrating an operation of a transforming switch according to an example embodiment.

FIG. 9 is a flow chart illustrating an operation of a transforming switch according to an example embodiment. The flow chart of FIG. 9 may be for an inbound message (a message from a client to a server) or for an outbound message (a message from a server to a client). The received message may first be decrypted by security accelerator 815, and then validated by validation accelerator 142 (FIG. 8).

Referring to FIG. 9, at block 910, the transformer 715 determines if the message requires a data transformation or not. If a transformation is required, the transforming switch 710 must determine which transform to perform on the data or message. If no transform is required, for example, if the message is already in a format that may be processed by the destination application or node, then the message is simply passed on to the message director 145 and switch 165, where the message is switched to one of a plurality of servers (or output ports) based on the business transaction information, an address, or other information, block 925.

If a transformation is required, a transformation template is retrieved, block 915. The transformation template provides instructions or code indicating how the transform should be performed. The transformation template is preferably retrieved from local storage, such as local memory or cache or local disk, if available locally, or from a remote location, for example, from another server via a network, if not locally available. The transformed message is then switched or output to a server or processing node.

Various embodiments of blocks 910 and 920 of the flow chart of FIG. 9 will now be described in greater detail.

For block 910 (FIG. 9), different types of fields or data in the received message can be examined in order to determine a type of transformation that is required (or which should be performed), if any. The transforming switch 710 may identify a transform to be performed on the basis of one or more of the following, for example:

a) Source address and port number of received message
b) Destination address and port number of received message
c) a program identifier—that identifies a program to process the message; for example, a request-line (the URL), such as a request line of a HTTP POST message, such as "POST www;acme.com/purchasing/order.cgi HTTP/1.1". This program identifier may correspond to a specific format. For example, maybe this particular program can process messages provided only in format A. Thus, this program identifier in the message may be used to identify the transformation that should be performed on the received message. For instance, in this example, if the received message was provided in format B, a transformation from format B to format A may be required.

d) a portion of validation instructions provided within the message: The validation instructions, such as a document type declaration, schema, etc., is an optional area of the document that declares the structure, element types, attributes, etc. of the validation template. To be a valid document, the structure and grammar of the application data in the document typically should match the structure and grammar defined by the validation template, for example, if validation instructions are included in the document. The validation template can be provided internal to (or within) the document and/or external to the document. Thus, examples of validation instructions that can be used to identify a transform for the message include:

1) a document format identifier or a reference to an external validation template, for example, a reference or URL to a DTD or schema for the message. An example would be the DOCTYPE statement "<DOCTYPE hogsforsale 'hogs.dtd'>, which identifies the type of document (hogsforsale) and identifies a validation template (e.g., DTD or schema) "hogs.dtd", that can be used to validate the document or message. Thus, if a transform is required, the transform would transform the message from the hogs.dtd format (or the hogsforsale format) to another format.

2) an internal validation template, such as a DTD or schema, such as the internal validation template 419 shown in FIG. 4.

e) one or more XML tags and/or the application data or business transaction information within the message or XML document which matches a predetermine pattern or value. A start tag <XML>, and </XML>, an end tag, identify the start and end, respectively, of the application data (or XML data). This indicates that the message is provided in XML format. The XML document or message includes markup characters (or tags) which describe data, and data characters. As an example, a "To" element of an XML document is written as: <To>bookstore.com</To>. Where<To> is a start Tag and </To> is an end tag, which are markup characters because they describe the XML data characters (bookstore.com). For example, maybe all transaction data to and from "Bookstore.com" are provided in format A, while all transaction data or message to and from "market.com" are provided in format B. Thus, tags or specific business transaction information can be used to identify that a corresponding transform should be used to transform certain messages. In this example, the "to: Bookstore.com" and "from: market.com" tags and data can be used to determine that "format B to format A" transformation template should be used to transform the message or data.

Or, if all servers or applications behind a switch 710 with a specific address/and/or port number are known by switch 710 to communicate messages only using format C. The switch 710 may then examine other information in the message or packet to determine the correct format transformation (including a transformation either to or from format C).

According to an example embodiment, a first pattern in a received message can be used to identify a transform to be performed on the message, while a second pattern in the message can be used to switch the message to a specific server (content based switching). For example, if a received XML message includes a tag that says "<AXML>," then this may indicate that the data is provided in AXML format. Let's also assume that Bookstore.com can process messages or transactions provided only in BXML format. Thus, if the "To" tag in the document says "To: Bookstore.com" (or if the destination address corresponds to Bookstore.com), then the transformer 715 will transform the message from AXML to BXML using an appropriate transformation template, such as an "AXML to BXML" transformation template. The reverse transformation would be used to transform any reply messages from Bookstore.com.

f) a field, such as a "User Agent" field in a HTTP message, that identifies the type of application or device that sent a message, such as a wireless device that can process messages in data format A, or a web browser that can process messages in data format B. These are just a couple of examples.

At block 920 (FIG. 9), transformer 715 (FIGS. 7–8) transforms at least a portion of a received message from a first data format to a second data format. There are many different ways in which this can be performed. According to one example, a transformation template is used that describes how the tags and data are transformed from one format to another format. An example of a transformation template is an XML Style Language Transform (XSLT). Here is one example that illustrates how a XSLT (or transformation template) can be used to perform a transformation.

The received message is provided in a TypeAxml format and needs to be transformed to a TypeBxml format. The start tag "<TypeAxml> indicates that this message is provided in TypeAxml format.

Here is the received message:
```
<? xml version="1.0"?>
<TypeAxml>
    <PurchaseOrder>
        <From>acme.com</From>
        <To>widgetmaker</To>
        <Part>
            <Partnumber>100-32323</Partnumber>
            <Description>Widget</Description>
            <Qty>3</Qty>
        </Part>
    </PurchaseOrder>
</TypeAxml>
```
Here is the XSLT stylesheet to transfrom a PurchaseOrder from TypeAxml into TypeBxml:
```
<xsl:stylesheet version="1.0"
xmlns:xsl="http://www.w3.org/1999/XSL/Transform">
<xsl:template match="/">
<? xml version="1.0"?>
<TypeBxml>
    <PurchaseOrder>
        <Sender><xsl:value-of select="//From"/></Sender>
        <Receiver><xsl:value-of select="//To"/></Receiver>
        <PartItem>
            <Number><xsl:value-of select="//Part/
            Partnumber"/></Number>
            <Description><xsl:value-of
select="//Part/Description"/></Description>
            <Qty>3</Qty>
        </PartItem>
    </PurchaseOrder>
</TypeBxml>
</xsl:template>
</xsl:stylesheet>
```
The transformed output message looks like this:

-continued

```
<? xml version="1.0"?>
<Type Bxml>
    <PurchaseOrder>
        <Sender>acme.com</Sender>
        <Receiver>widgetmaker</Receiver>
        <PartItem>
            <Number>100-32323</Number>
            <Description>Widget</Description>
            <Qty>3</Qty>
        </PartItem>
    </PurchaseOrder>
</TypeBxml>
```

In this example some of the element names from TypeAxml need to be transformed or converted to the element names that are compatible with TypeBxml.

From TypeAxml, element <From> needs to be converted to TypeBxml element <Sender>

From TypeAxml, element <To> needs to be converted to TypeBxml element <Receiver>

From TypeAxml, element <part> needs to be converted to TypeBxml element<partItem>

From TypeAxml, element <Partnumber> needs to be converted to TypeBxml element <Number>

In this example none of the data or values corresponding to the transformed elements are changed, just the element names (or tags) are changed. Also, note that the first start tag <TypeAxml> needs to be converted to <TypeBxml>. Similarly, the end tag </TypeAxml> needs to be converted to </TypeBxml>. This change will indicate to the application server that the message is in the proper format for processing.

Figure 10:
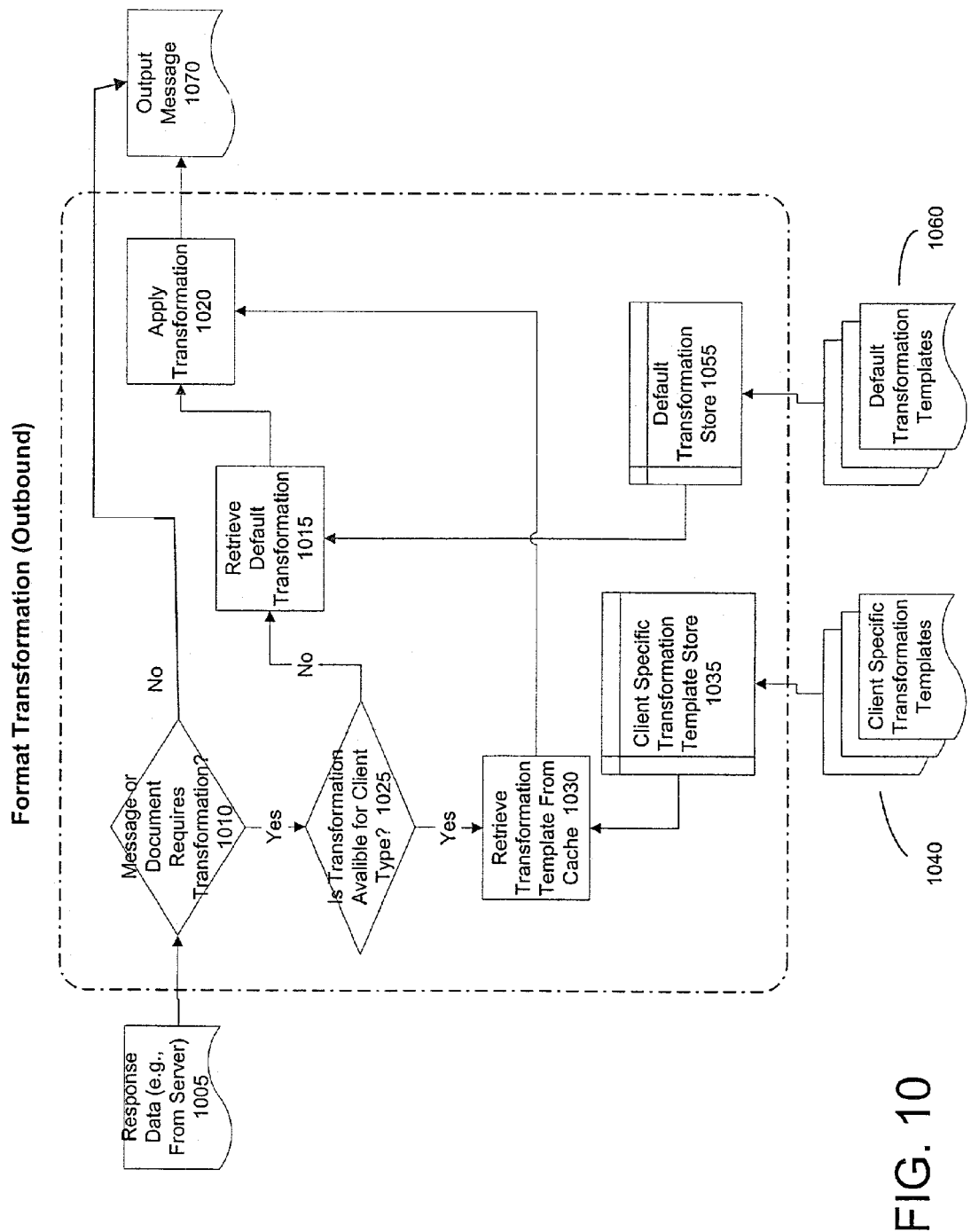
FIG. 10 is a flow chart illustrating an operation of a transforming switch according to another example embodiment.

FIG. 10 is a flow chart illustrating an operation of a transforming switch according to another example embodiment, such as an inbound request to a server, and the outbound response from the server back to a client.

In this example of FIG. 10, a request for information may be submitted by a client to a server, for example, via transforming switch 710. For example, this request may be a request for a stock quote from a web browser. The request is received by the application server, the data is obtained from a database coupled to the application server. The application server then creates an XML response message providing the requested stock quote (for example). At block 1005, this response message (e.g., an XML message) is received at transforming switch 710.

At block 1010, the transforming switch determines the type of transform that is required, if any. If no transform is required, the message is then switched or output, block 1070. In this example, because the initial request arrived at the transforming switch 710 from an HTML application (e.g., based on a header of the stock quote request indicating HTML, or the User Agent indicating an HTML application submitted the original request, etc.), the transforming switch 710 determines that a XML to HTML transform is required.

At block 1025, a determination is made as to whether the (client-specific) transformation template is available to perform the corresponding transformation. If the requested (or client-specific) transformation template is not available, then a default transformation template is retrieved either from a local store 1055 or from a remote location 1060. This default transformation is then used to transform the response message, block 1020.

If the requested (client-specific) transformation template is available, the client-specific (or requested) transformation template is retrieved from a local store if available, block 1035, or from a remote location (e.g., retrieved from a server via a network) if not locally available, block 1040.

The retrieved transformation template is then used to transform the response message, block 1020. The transformed message is then output to the network 130 for routing back to the requesting client application, block 1070.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. An apparatus comprising:
    a transformer to transform a message from a first format to a second format and to transform a reply to the message from the second format to the first format, at least one of the first format and the second format comprising an XML format defining a document type;
    a switch to switch the transformed message to a selected processing node; and
    a message director to connect to the transformer and the switch, the message director to make a switching decision for the message based upon application data in the message, and output the switching decision to the switch.

2. The apparatus of claim 1 wherein the apparatus comprises a transforming switch.

3. The apparatus of claim 1 wherein the transformer selects a transformation template to transform the message based on one or more of the following in the message matching a predetermined pattern or value:
    an address and/or port number in the message;
    a request line or an identification of an application to process a portion of the message;
    a root element or a root tag or other information that describes the content of the message;
    a validation template or a reference to a validation template;
    one or more XML tags; and
    business transaction information.

4. The apparatus of claim 3 wherein if the message is transformed based on the validation template or a reference to a validation template then said validation template comprises either a Document Type Definition (DTD) or a schema.

5. The apparatus of claim 1 wherein the apparatus is a transforming switch coupled between a network and a plurality of servers or processing nodes.

6. The apparatus of claim 1 wherein the transformer transforms the message from one or more of the following:
    HTML to XML;
    XML to HTML;
    XML to EDI;
    EDI to XML;
    XML to ASCII flat file;
    ASCII flat file to XML;
    ASCII flat file to EDI; and
    EDI to ASCII flat file.

7. The apparatus of claim 1 and further comprising a security accelerator to encrypt and/or decrypt messages.

8. The apparatus of claim 1 and further comprising a validator coupled to the transformer to validate received messages based on one or more validation templates.

9. A method comprising:
receiving a message;
determining if a transformation should be performed on the message;
performing the following if the transform should be performed:
   identifying a transform template, based upon a first portion of the message, to be used to transform the message; and
   transforming the message from a first format to a second format and transforming a reply to the message from the second format to the first format using the identified transform template, at least one of the first format and the second format comprising a an XML format defining a document type; and
switching the message, based upon a second portion of the message, to a selected server or processing node.

10. The method of claim 9 wherein the first portion of the message comprises one or more of the following:
an address and/or port number in the message;
a request line or an identification of an application to process a portion of the message;
a root element or a root tag or other information that describes the content of the message;
a validation template or a reference to a validation template;
one or more XML tags; and
business transaction information.

11. The method of claim 9 wherein the second portion of the message comprises one or more of the following:
an address and/or port number in the message;
a request line or an identification of an application to process a portion of the message;
a root element or a root tag or other information that describes the content of the message;
a validation template or a reference to a validation template;
one or more XML tags; and
business transaction information.

12. A method comprising:
receiving a message;
determining if a transformation should be performed on the message;
performing the following if the transform should be performed:
   identifying a transform template to be used to transform the message, the identifying based upon a root element or a root tag or other information that describes the content of the message, and/or a validation template or a reference to a validation template;
   transforming the message from, a first format to a second format and transforming a reply to the message from the second format to the first format using the identified transform template, at least one of the first format and the second format comprising an XML format defining a document type; and
   switching the message to a selected server or processing node based upon a portion of the message.

13. The method of claim 12 and further comprising validating the received message.

14. The method of claim 13 and wherein the validating comprises either removing validation instructions from the message and/or adding an indication that the message has been pre-validated.

15. The method of claim 12 wherein the switching comprises switching the message to a selected server or processing node based on tags and/or business transaction information within the message.

16. An apparatus comprising a media having instructions thereon, the instructions resulting in the following when executed:
receiving a message;
determining if the message should be transformed;
performing the following if the message should be transformed:
   identifying a transform template to be used to transform the message based on a first portion of the message; and
   transforming the message from a first format to a second format and transforming a reply to the message from the second format to the first format using the identified transform template, at least one of the first format and the second format comprising an XML format defining a document type; and
   switching the message to a selected server or processing node based an a second portion of said message.

* * * * *

UNITED STATES PATENT AND TRADEMARK OFFICE
CERTIFICATE OF CORRECTION

PATENT NO. : 7,111,076 B2  Page 1 of 1
APPLICATION NO. : 09/741807
DATED : September 19, 2006
INVENTOR(S) : Abjanic et al.

It is certified that error appears in the above-identified patent and that said Letters Patent is hereby corrected as shown below:

On the Title page, in field (56), under "U.S. Patent Documents", in column 2, line 10, after "6,772,413" delete "B1" and insert -- B2 --, therefor.

On the Title page, in field (56), under "Foreign Patent Documents", in column 2, line 1, after "9/2000" insert -- H04Q 07/22 --.

On the Title page, in field (56), under "Other Publications", in column 2, line 7, delete "Achitecture,"" and insert -- Architecture," --, therefor.

In column 19, line 14, in Claim 9, after "comprising" delete "a".

In column 20, line 8, in Claim 12, delete "from," and insert -- from --, therefor.

In column 20, line 43, in Claim 16, delete "an" and insert -- on --, therefor.

Signed and Sealed this

Eighth Day of April, 2008

JON W. DUDAS
*Director of the United States Patent and Trademark Office*